United States Patent
Bookwalter et al.

(10) Patent No.: US 6,620,097 B1
(45) Date of Patent: Sep. 16, 2003

(54) THREE-DIMENSIONAL TILT RATCHET MECHANISM

(75) Inventors: John R. Bookwalter, Brattleboro, VT (US); Rene Cabrera, Stoughton, MA (US); John McMorrow, Franklin, MA (US); Kyle Moore, Acushnet, MA (US); Nelson Torres, Rochester, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 0 days.

(21) Appl. No.: 10/113,801

(22) Filed: Mar. 29, 2002

(51) Int. Cl.[7] .................................................. A61B 1/32
(52) U.S. Cl. ...................................... 600/231; 600/233
(58) Field of Search ................................. 600/201, 210, 600/213, 226, 227, 228, 231, 232, 233, 234, 204, 205, 209, 225, 229

(56) References Cited

U.S. PATENT DOCUMENTS

| | | | |
|---|---|---|---|
| 4,254,763 A | | 3/1981 | McCready et al. |
| 4,424,724 A | | 1/1984 | Bookwalter et al. |
| 5,375,481 A | | 12/1994 | Cabrera et al. |
| 5,902,233 A | * | 5/1999 | Farley et al. ............... 600/213 |
| 6,241,659 B1 | * | 6/2001 | Bookwalter et al. ........ 600/231 |
| 6,371,911 B1 | * | 4/2002 | Hossain et al. ............. 600/232 |
| 6,431,025 B1 | * | 8/2002 | Koros et al. .............. 74/577 M |
| 6,530,883 B2 | * | 3/2003 | Bookwalter et al. ........ 600/231 |
| 2002/0177752 A1 | * | 11/2002 | Dobrovolny ................ 600/226 |
| 2003/0004401 A1 | * | 1/2003 | Ball et al. ................... 600/233 |

* cited by examiner

Primary Examiner—Cary E. O'Connor
Assistant Examiner—David Austin Bonderer
(74) Attorney, Agent, or Firm—Nutter McClennen & Fish LLP

(57) ABSTRACT

A three-dimensional tilt ratchet mechanism that is able to rotate, pivot, and bend forwards or backwards with ease is provided. The mechanism includes a device for multi-dimensional movement and placement of a retractor blade which comprises a first member adapted to receive a stem of a retractor blade. The first member has a locking mechanism effective to enable selective lateral adjustment of the retractor blade relative to the first member. Also provided is a second member to which the first member is mated. The first member is vertically pivotable with respect to the second member to enable selective vertical pivoting adjustment of the retractor blade relative to the second member. A rotator indexing body is mated to the second member and is adapted to mount onto a rim of a surgical support. The second member is rotatable with respect to the rotator indexing body such that the first member, the second member and the retractor blade are able to selectively rotate about the longitudinal axis of the rotator indexing body.

16 Claims, 11 Drawing Sheets

SECTION A-A

SECTION B-B

SECTION C-C

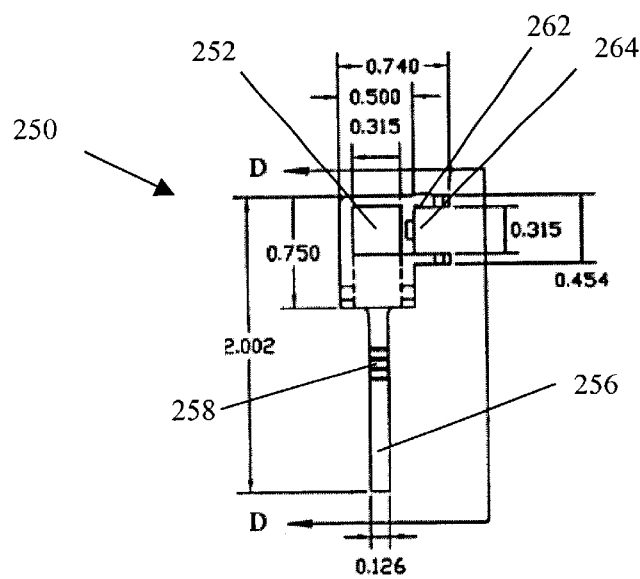
FIG. 6A
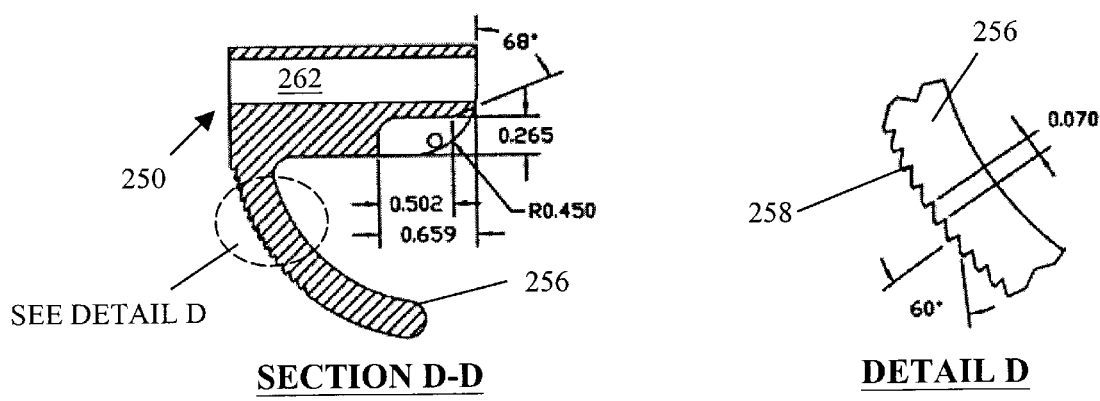
SECTION D-D
FIG. 6B
DETAIL D
FIG. 6C

THREE-DIMENSIONAL TILT RATCHET MECHANISM

CROSS-REFERENCE TO RELATED APPLICATIONS

Not applicable.

STATEMENT REGARDING FEDERALLY SPONSORED RESEARCH

Not applicable.

FIELD OF THE INVENTION

The present invention relates generally to a multi-position ratchet mechanism for holding a surgical retractor blade and, more particularly, a three-dimensional ratchet mechanism which permits the retractor blade to be tilted into the wound and retracted at the same time while also enabling angular adjustment of the retractor blade to facilitate deployment in deep wounds.

BACKGROUND OF THE INVENTION

In surgical operations of the chest or abdomen, it is often necessary to use a retraction apparatus to retain tissue away from the operative site. Typically, the retraction apparatus includes a housing member configured to lock onto a circumferential ring located above the operative site. To maintain the ring in a fixed position, the ring can be connected to a support post adjacent to the site. An extension arm may be attached to the support post for supporting the circumferential ring. Within the housing member a retraction blade can usually be found for grabbing the tissue around the surgical incision. The housing member can also include a ratcheting mechanism and/or a tilting mechanism to draw the retraction blade away from the incision, thereby effecting the pulling away and/or lifting of the tissue around the incision to expose the desired surgical area. Examples of such retractor systems are disclosed in U.S. Pat. Nos. 4,254,763, 4,424,724 and 5,375,481.

Yet despite these retraction systems, there continues to be a need for a retraction system which can provide the retractor blade with even more flexibility of movement for use in deep wounds. It would therefore be advantageous to have a ratchet mechanism which can not only enable the tilt and the movement of the retractor blade in and out of the wound site, but also the angular adjustment, or rotation, of the retractor blade without having to remove the ratchet from the ring. The ability to rotate or tilt the retractor blade as well provides the surgeon with even greater control over the exposure of the surgical area.

SUMMARY OF THE INVENTION

The present invention achieves the aforementioned goals by providing a three-dimensional tilt ratchet mechanism that is able to rotate, pivot, and bend forwards or backwards with ease. The present invention provides a device for multi-dimensional movement and placement of a retractor blade which comprises a first member adapted to receive a stem of a retractor blade. The first member has a locking mechanism effective to enable selective lateral adjustment of the retractor blade relative to the first member. Also provided is a second member to which the first member is mated. The first member is vertically pivotable with respect to the second member to enable selective vertical pivoting adjustment of the retractor blade relative to the second member. A rotator indexing body is mated to the second member and is adapted to mount onto a rim of a surgical support. The second member is rotatable with respect to the rotator indexing body such that the first member, the second member and the retractor blade are able to selectively rotate about the longitudinal axis of the rotator indexing body.

In one aspect of the present invention, the second member is rotatable up to approximately 30 degrees about the longitudinal axis of the rotator indexing body. The device further includes a ratchet release bar pivotally connected to the second member for adjustably maintaining the retractor blade a fixed vertical distance from the second member. The locking mechanism can comprise a spring biased pawl, and a ball plunger assembly is included on the rotator indexing body for achieving an interference fit between the rotator indexing body and the rim of the surgical support. To fix the rotator indexing body in a fixed position with respect to the second member, the rotator indexing body includes a plurality of indents extending circumferentially about the rotator indexing body that are engaged by a locking pin extending from the second member.

In one exemplary embodiment of the present invention, the device comprises a retractor blade holder having an opening therein for receiving a retractor blade and a curved ratchet extending therefrom. A pawl is pivotally connected to the retractor blade holder and adjustably maintains the retractor blade a fixed distance from the retractor blade holder. The retractor blade holder is pivotally connected to a housing member that includes a channel for insertion of the curved ratchet therethrough. A ratchet release bar pivotally connected to the housing member enables the retractor blade holder to be adjustably maintained a fixed distance from the housing member. The housing member includes an opening configured to receive and rotatably hold a rotating indexer. The rotating indexer has a slot therein for attaching to a ring secured to a stationary post, and further includes a plurality of indents extending circumferentially about the rotating indexer. A locking pin is provided which extends from the housing member to engage the plurality of indents to maintain the rotating indexer in a fixed angle with respect to the housing member.

In one aspect of the exemplary embodiment, the curved ratchet includes a plurality of teeth and the ratchet release bar includes an undercut engageable with the plurality of teeth on the curved ratchet. The ratchet release bar can include a thumb release tab for ease of manipulation. A spring coil is provided for biasing the pawl to a desired position, and for applying a spring force against the ratchet release bar. Further, an indexer coil is provided with the rotating indexer to maintain a spring bias force on the rotating indexer while held inside the housing member. The ratchet device of the present invention also includes a ball plunger assembly on the rotating indexer for achieving an interference fit between the rotating indexer and an attached ring. The ball plunger assembly can comprise a spring coil having a threaded end and a ball at an opposite end.

Further features of the invention, its nature and various advantages, will be more apparent from the accompanying drawings and the following detailed description of the drawings and the preferred embodiments.

BRIEF DESCRIPTION OF THE DRAWINGS

The invention can be more fully understood from the following detailed description taken in conjunction with the accompanying drawings, in which:

FIG. 6A is a front view of the retractor blade holder of FIG. 2;

FIG. 6B is a cross-sectional view of the retractor blade holder of FIG. 6A along lines D—D;

FIG. 6C is a detailed view of the curved ratchet of FIG. 6B;

FIG. 8 is a side view, partially cut away, of the ratchet mechanism of FIG. 7 with the ratchet toed-in;

DETAILED DESCRIPTION OF THE DRAWINGS

Figure 1:
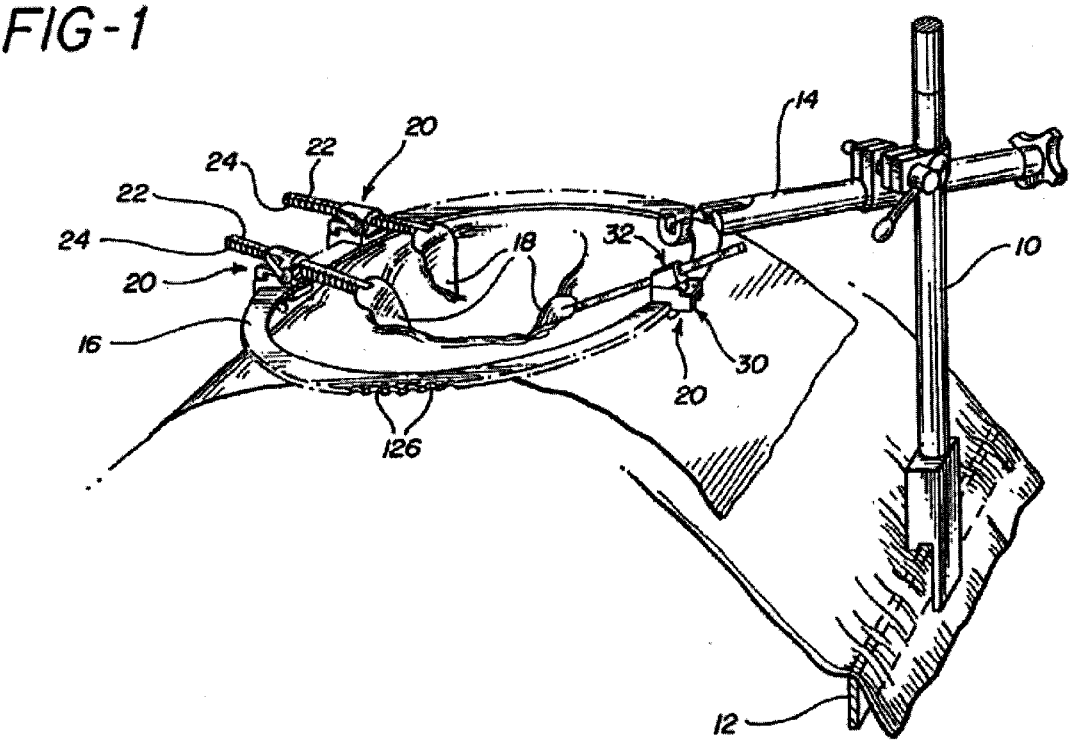
FIG. 1 is a perspective view of an entire retractor assembly with which a multi-position ratchet mechanism of the prior art is used.

Referring now to FIG. 1, there is shown a surgical retractor assembly similar to the one disclosed in U.S. Pat. No. 5,375,481, which is hereby incorporated by reference. A vertical support post 10 is clamped to the side rail 12 of an operating table on which the patient is supported. A horizontal arm 14 extends horizontally over the patient and supports a support ring 16 on which a number of retractor blades 18 are supported by ratchet mechanisms 20. Each retractor blade 18 includes a generally rectangular stem 22 along one side of which is included a ratchet 24. Retractor blades 18 extend into the wound cavity. The ratchet mechanisms 20 are contained within housing members 30 that can attach to indentations 126 on the support ring 16. A pivoting housing member 32 connected to each of the housing members 30 enables the retractor blade 18 to tilt with respect to the circumferential ring 16. The ratchet mechanism of the present invention and the-ratchet mechanism disclosed in U.S. Pat. No. 5,375,481 allow the surgeon to retract and lift an organ at the same time to duplicate the natural "toed-in" method of retraction that can be achieved by hand.

The ratchet device of the present invention provides the additional benefit of enabling an attached retractor blade to move forwards or backwards, pivot forward or backward (toed-in or toed-out), and rotate left or right up to about 30 degrees, i.e., in three dimensions or in three planes. Provided is a device for multi-dimensional movement and placement of a retractor blade which comprises a first member adapted to receive a stem of a retractor blade. The first member has a locking mechanism effective to enable selective lateral adjustment of the retractor blade relative to the first member. Also provided is a second member to which the first member is mated. The first member is vertically pivotable with respect to the second member to enable selective vertical pivoting adjustment of the retractor blade relative to the second member. A rotator indexing body is mated to the second member and is adapted to mount onto a rim of a surgical support. The second member is rotatable with respect to the rotator indexing body such that the first member, the second member and the retractor blade are able to selectively rotate about the longitudinal axis of the rotator indexing body.

Figure 2:
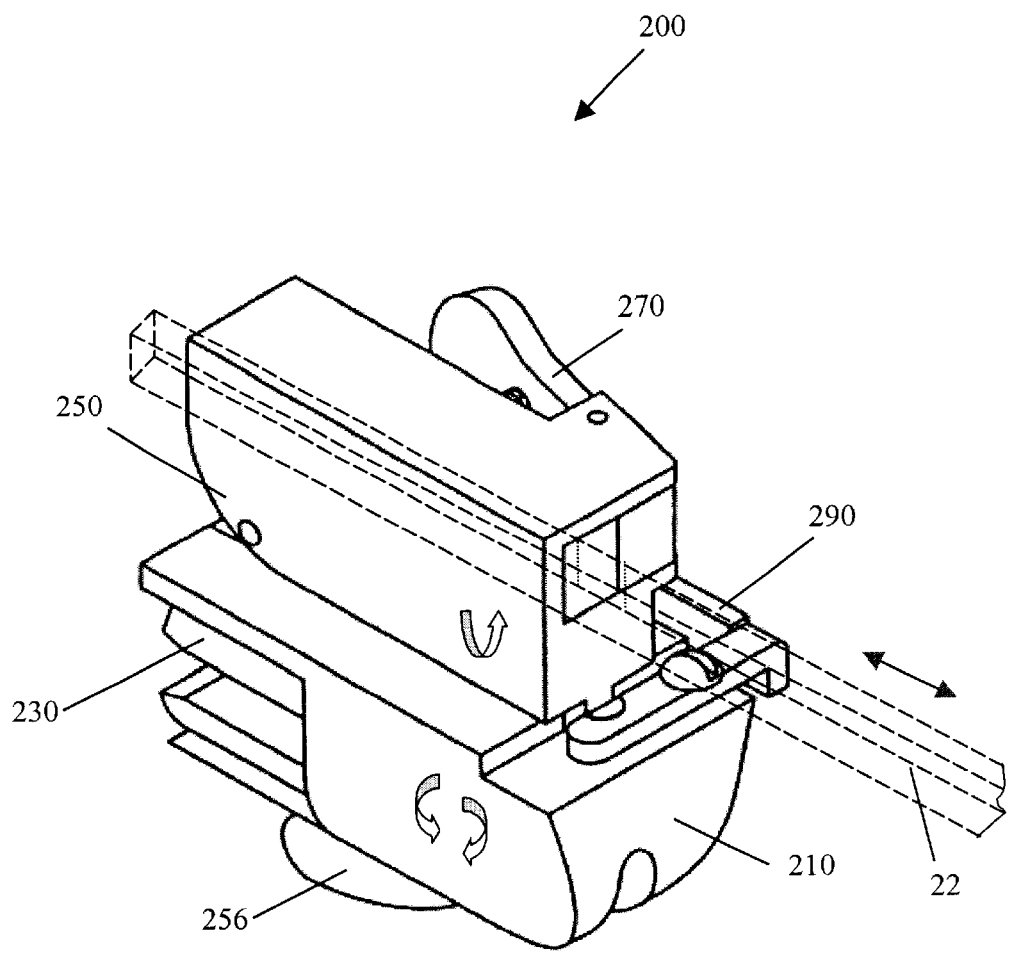
FIG. 2 is a perspective view of a three-dimensional tilt ratchet mechanism of the present invention.

FIG. 2 illustrates a perspective view of a tilt ratchet mechanism 200 having these features, in which there is provided a housing member 210 configured to hold a rotating indexer 230 therein. A retractor blade holder 250 is pivotally connected to housing member 210 and is adapted to retain a retractor blade 18 with an attached elongate ratcheted stem 22 (shown in phantom) similar to the one depicted in FIG. 1. As the bidirectional arrow suggests, the retractor blade 18 and attached elongate ratcheted stem 22 can be moved towards or away from the retractor blade holder 250 and fixed at this specific distance with spring-biased pawl 270. Meanwhile, retractor blade holder 250 can also be vertically pivoted up and down as indicated by the arrow, that is, towards or away from housing member 210 to effect the vertical position of the retractor blade 18, and fixed in place with ratchet release bar 290. Finally, rotating indexer 230 and housing member 210 are rotatable with respect to one another to effect angular adjustment of the retractor blade 18 and attached stem 22. In accordance with the left and right arrows, housing member 210 is rotatable about the longitudinal axis of rotating indexer 230.

Figure 3:
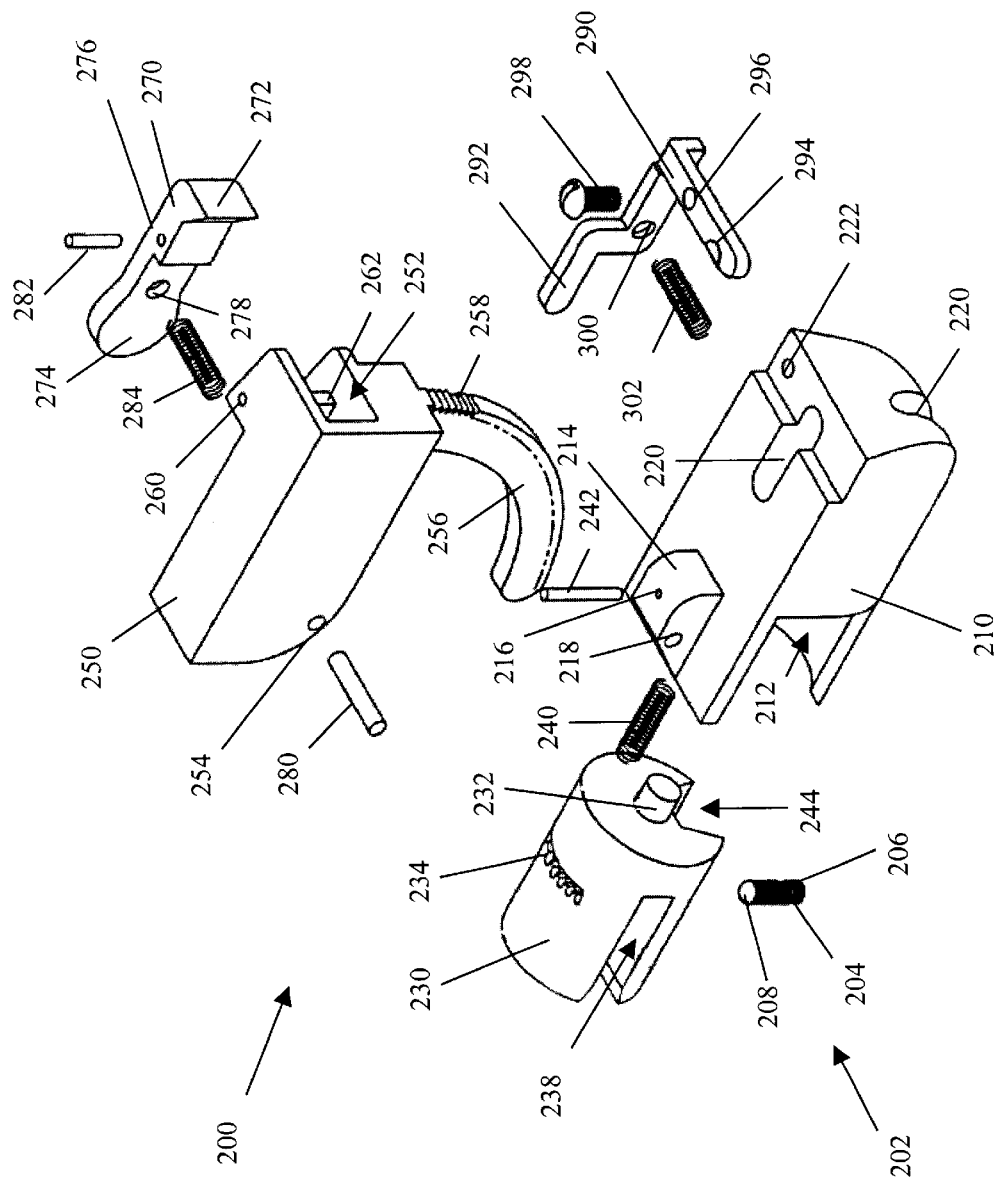
FIG. 3 is an exploded view of the ratchet mechanism of FIG. 2.

To understand how the tilt ratchet mechanism 200 of the present invention achieves three-dimensional adjusting and positioning of an attached retractor blade 18 and ratcheted stem 22, an exploded view of the tilt ratchet mechanism 200 is provided in FIG. 3. Housing member 210 shown in FIGS. 4A and 4B includes an indexer receiving opening 212 configured in size and shape to receive rotating indexer 230, and a ramp 214 for creating a hinged or pivoting connection with retractor blade holder 250. The rotating indexer 230 includes a protrusion 232 also illustrated in FIGS. 5A–5D over which is placed indexer spring coil 240. As shown, indexer receiving opening 212, rotating indexer 230, and protrusion 232 can be substantially cylindrical in shape and sized so that rotating indexer 230 is capable of rotating within housing member 210 without interference. Inside housing member 210 is a coil receiving notch (not shown) for receiving the free end of indexer spring coil 240. Indexer spring coil 240 is longer than protrusion 232 such that rotating indexer 230 is subject to a spring force in a lateral direction when rotating indexer 230 and indexer spring coil 240 are placed within housing member 210 and seated within the coil receiving notch, thereby enabling rotating indexer 230 to be slightly moved in or out of the housing member 210 against the spring force bias with manual manipulation.

A slot 238 on rotating indexer 230 enables the ratchet mechanism 200 to be attached to a circumferential ring 16 in a manner similar to that depicted in FIG. 1. As shown in FIG. 5D, slot 238 can be slightly flared. A ball plunger assembly 202 comprising a spring actuated plunger 204 and ball 208 is provided within the rotating indexer 230 for achieving an interference fit between the tilt ratchet mechanism 200 and ring 16 for securing the ratchet mechanism 200 to the ring 16. Plunger 204 can comprise a spring coil having a threaded end 206 for threading onto threaded bore 224 of housing member 210 shown in FIG. 4B. The plunger 204 and attached ball 208 are configured to extend through an aperture (not shown) within rotating indexer 230 so that a portion of the ball plunger assembly 202 protrudes from housing member 210 through slot 238 of the rotating indexer 230. In this manner, ball plunger assembly 202 also helps maintain rotating indexer 230 within housing member 210. When ring 16 is placed into slot 238 of rotating indexer 230, ball plunger assembly 202 can be seated against one of the indentations 126 on the ring 16, locking the tilt ratchet mechanism 200 onto the ring. Removal of the tilt ratchet mechanism 200 can easily be accomplished by applying a force against the rotating indexer 230 to depress the plunger 204 and unseat the ball 208 from the indentation 126 so that the ring 16 can slide out of slot 238. The height of ball plunger assembly 202 can be adjusted from within threaded bore 226, as necessary.

Figure 5A:
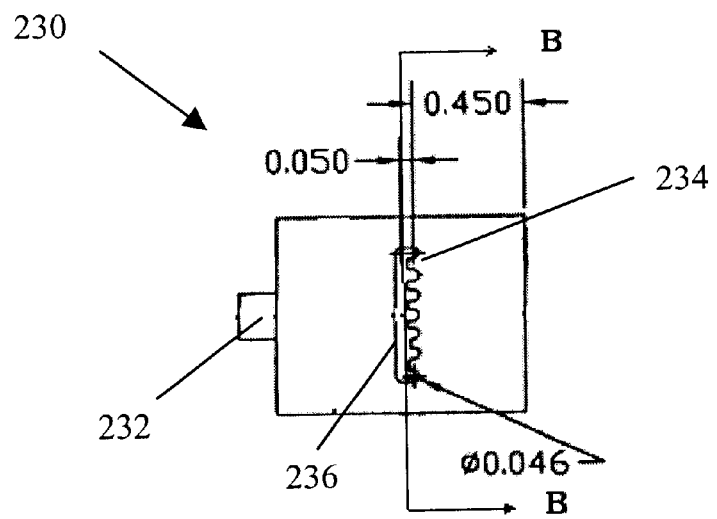
FIG. 5A is a top-down view of the rotating indexer of FIG. 2.
Figure 5B:
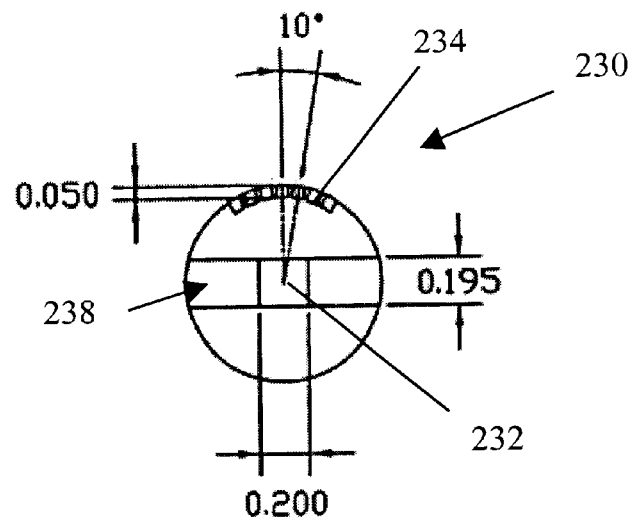
FIG. 5B is a cross-sectional view of the rotating indexer of FIG. 5A along lines B—B.

To enable rotating indexer 230 to rotate and maintain an angular position within housing member 210, a plurality of indents 234 are provided on rotating indexer 230 as illustrated in detail in FIGS. 5A and 5B. The plurality of indents 234 are connected by a common trench 236 and extend in a row in a circumferential direction along a surface of the rotating indexer 230, with each of the indents 234 being spaced approximately 10 degrees apart from an adjacent indent. An individual indent 234 can be engaged by an indexer pin 242 mounted through a longitudinally extending indexer pin bore 216 on housing member 210 as shown in FIG. 3. The spring force exerted by indexer spring coil 240 enables rotating indexer 230 to be easily pushed in or out so that indexer pin 242 can stay in a specific indent 234 or slide into another indent 234.

As configured, the rotating indexer 230 can be rotated in increments of approximately 10 degrees up to about 30 degrees to the left or to the right with respect to the plane of the circumferential ring 16, to the left or right of plane perpendicular to midpoint of rotating indexer 230. The retraction force applied to the retractor blade 18 in FIG. 1 will push the rotating indexer 230 into the encapsulating housing member 210 and allow the indexer pin 242 to engage one of the indents 234, locking the rotating indexer 230 in the desired angle. Thus, the tilt ratchet mechanism 200 of the present invention can be rotated or angled up to about 30 degrees to the left or right with respect to the plane of the ring 16. Such features permit a closer duplication of the original function of a toed-in hand held retractor and greatly facilitates deployment of retractor blades in deep wounds and against bone. In addition, blade exchange and blade removal for the wound is also facilitated without removing the tilt ratchet mechanism 200 from the ring 16.

Retractor blade 18 and attached ratcheted stem 22, such as the ones illustrated in FIG. 1, are connected to the tilt ratchet mechanism 200 of the present invention by means of a retractor blade holder. As further shown in FIGS. 6A and 6B, retractor blade holder 250 can be configured with stem receiving opening 252 extending lengthwise for insertion of the ratcheted stem 22. Stem receiving opening 252 can comprise a through-hole as depicted in FIG. 6B, though it is not necessary for stem receiving opening 252 to extend all the way through the retractor blade holder 250.

To control the movement of the retractor blade 18 and attached ratcheted stem 22 into and out of the retractor blade holder 250 and hence the surgical site, tilt ratchet mechanism 200 can also include a spring biased pawl 270. As illustrated in FIG. 3, pawl 270 includes at one end a chamfered edge 272 for engaging the teeth 24 of the ratcheted stem 22, and at an opposite end a thumbpiece 274 for manually actuating the pawl 270. Pawl 270 is pivotally connected, or hinged, to retractor blade holder 250 by means of pawl pivot pin 282 which is inserted through bore 276 on pawl 270 and bore 260 on retractor blade holder 250. A pawl spring coil 284 situated between pawl 270 and a sidewall 262 bordering stem receiving opening 252 exerts a spring bias force on pawl 270 against sidewall 262. A coil receiving notch 278 on pawl 270 is configured to receive one end of pawl spring coil 284, while the other end is received in coil receiving notch 264 on sidewall 262 as shown in FIG. 6A. Collectively, the pawl spring coil 284 and pawl pivot pin enable retractor blade 18 and attached ratcheted stem 22 placed within the retractor blade holder 250 to be moved forwards or backwards and to be locked a fixed distance relative to the retractor blade holder 250 with precision and ease.

Figure 4A:
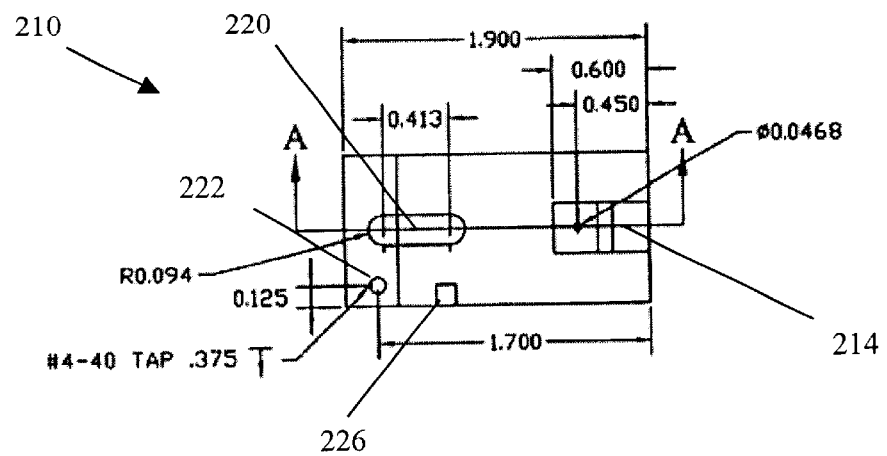
FIG. 4A is a top-down view of the housing member of FIG. 2.
Figure 4B:
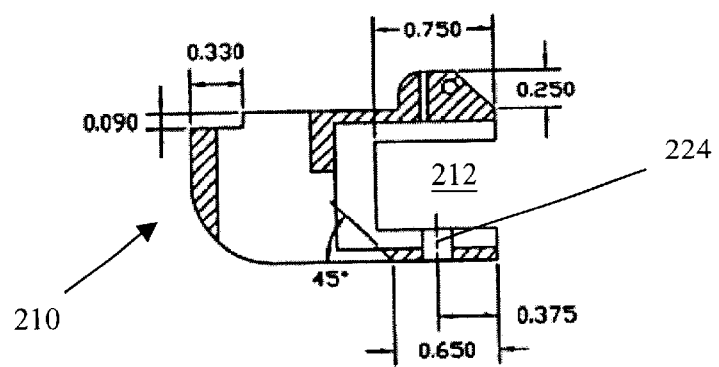
FIG. 4B is a cross-sectional view of the housing member of FIG. 4A along lines A—A.
Figure 5C:
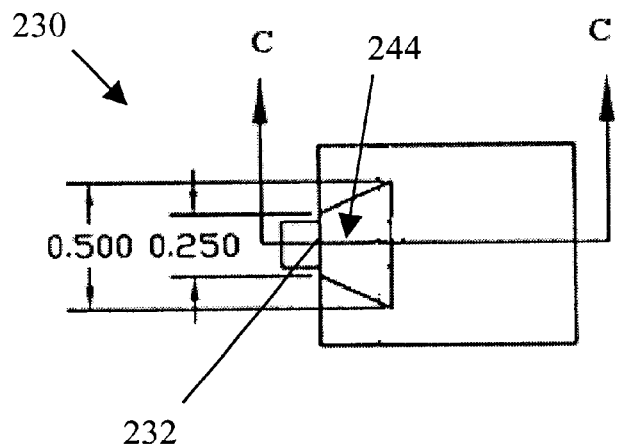
FIG. 5C is a bottom-up view of the rotating indexer of FIG. 2.
Figure 5D:
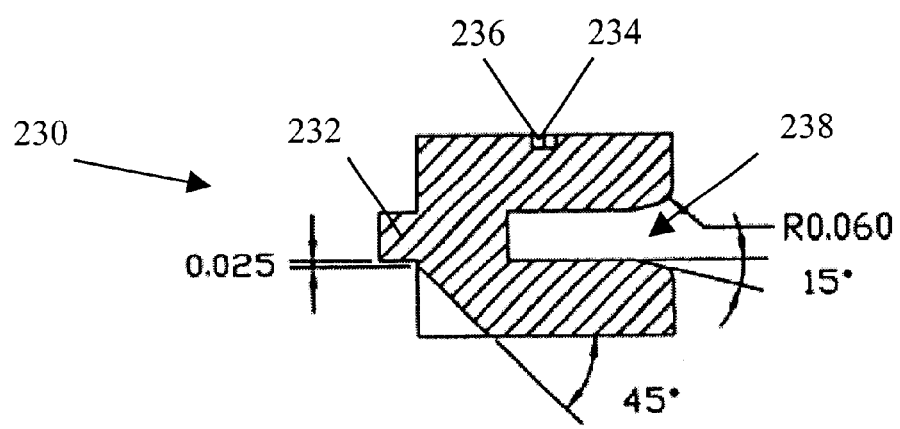
FIG. 5D is a cross-sectional view of the rotating indexer of FIG. 5C along lines C—C.

To effect the forwards or backwards tilting (toed-in or toed-out positions) of the retractor blade 18 and ratcheted stem 22 attached thereto, retractor blade holder 250 can be pivotally attached to housing member 210. A pivoting hinge or connection can be created by inserting retractor blade pivot pin through bore 254 on retractor blade holder 250 and through bore 218 extending laterally across ramp 214 of the housing member 210. Extending from retractor blade holder 250 is curved ratchet 256. A channel 220 is provided within housing member 210 to provide sufficient clearance for curved ratchet 256 to extend therethrough. As shown in FIG. 4A, channel 220 can be shaped like an oval in cross-section to enable curved ratchet 256 sufficient room to move up and down and extends all the way through housing member 210. Rotating indexer 230 is likewise provided with a cutaway portion 244 as illustrated in FIG. 5C for curved ratchet 256 to pass through. Cutaway portion can have angled sides resembling a trapezoid to accommodate curved ratchet 256 even when rotating indexer 230 is angled with respect to housing member 210.

Curved ratchet 256 can be provided with a plurality of teeth 258 on at least a portion thereof. Teeth 256 can be spaced approximately 60 degrees apart from one another, as depicted in FIG. 6C. A ratchet release bar 290 connected to housing member 210 can be provided for maintaining curved ratchet 256 of the retractor blade holder 250 at a fixed position relative to housing member 210. Thus, curved ratchet 256 can be fixedly positioned so as to be "toed-in" or "toed-out," that is, in the "toed-in" position, the free end of curved ratchet 256 is tilted towards the ring 16 with respect to retractor blade holder 250. In the "toed-out" position, the free end of curved ratchet 256 is tilted away from the ring 16 with respect to housing member 210.

As shown in FIG. 3, ratchet release bar 290 can be bent to provide a thumb release tab 292 at one end for manual actuation of the ratchet release bar 290. Ratchet release bar 290 also includes a grooved, or undercut region 294 for engaging the teeth 258 of curved ratchet 256. Ratchet release bar 290 is pivotally attached to housing member 210 by pivot screw 298 and spring biased against housing member 210 by ratchet release bar spring coil 302. A hinged or pivoting connection is created by inserting pivot screw 298 through bore 296 of ratchet release bar 290 and bore 222 on housing member 210. To exert a spring bias force against ratchet release bar 290, one end of ratchet release bar spring coil 302 is placed within coil receiving notch 300 on ratchet release bar 290 and the other end is placed within coil receiving notch 226 on housing member 210 as shown in FIG. 4A. Thus, with ratchet release bar 290, the tilting and locking of retractor blade holder 250 with respect to housing member 210 can be accomplished with ease by manually actuating thumb release tab 292.

Figure 7:
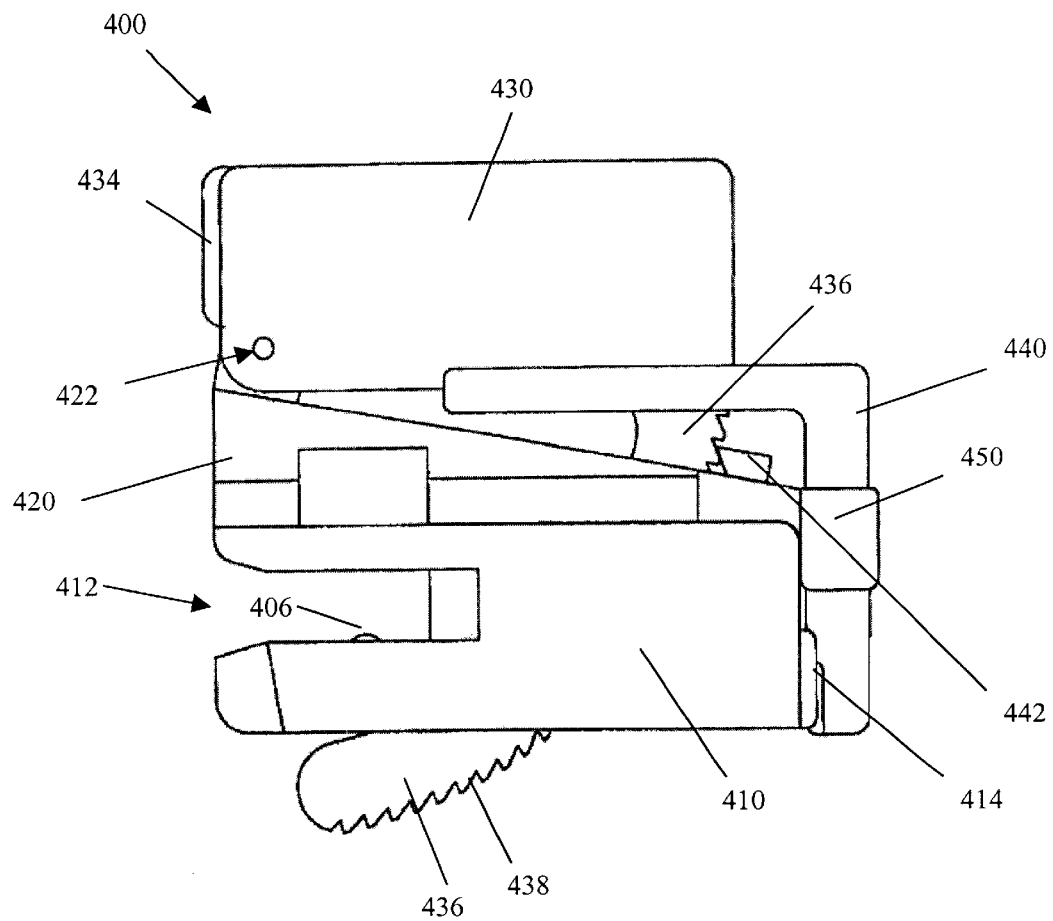
FIG. 7 is a side view of another exemplary embodiment of the three-dimensional tilt ratchet mechanism of the present invention.

FIG. 7 illustrates another exemplary embodiment of the present invention, in which tilt ratchet mechanism 400 includes a base member 410 supporting a ratchet holder 420 having attached thereto a ratchet housing 430. A slot 412 on base member 410 enables the ratchet mechanism 400 to be attached to a circumferential ring 16 in a manner similar to that depicted in FIG. 1. A spring actuated pin assembly 402 comprising a spring 404 and pin 406 illustrated in FIG. 8 is provided within the base member 410 for engaging one of the indentations 126 on the ring 16 to enable the ratchet mechanism 400 to be secured to ring 16.

Figure 8:
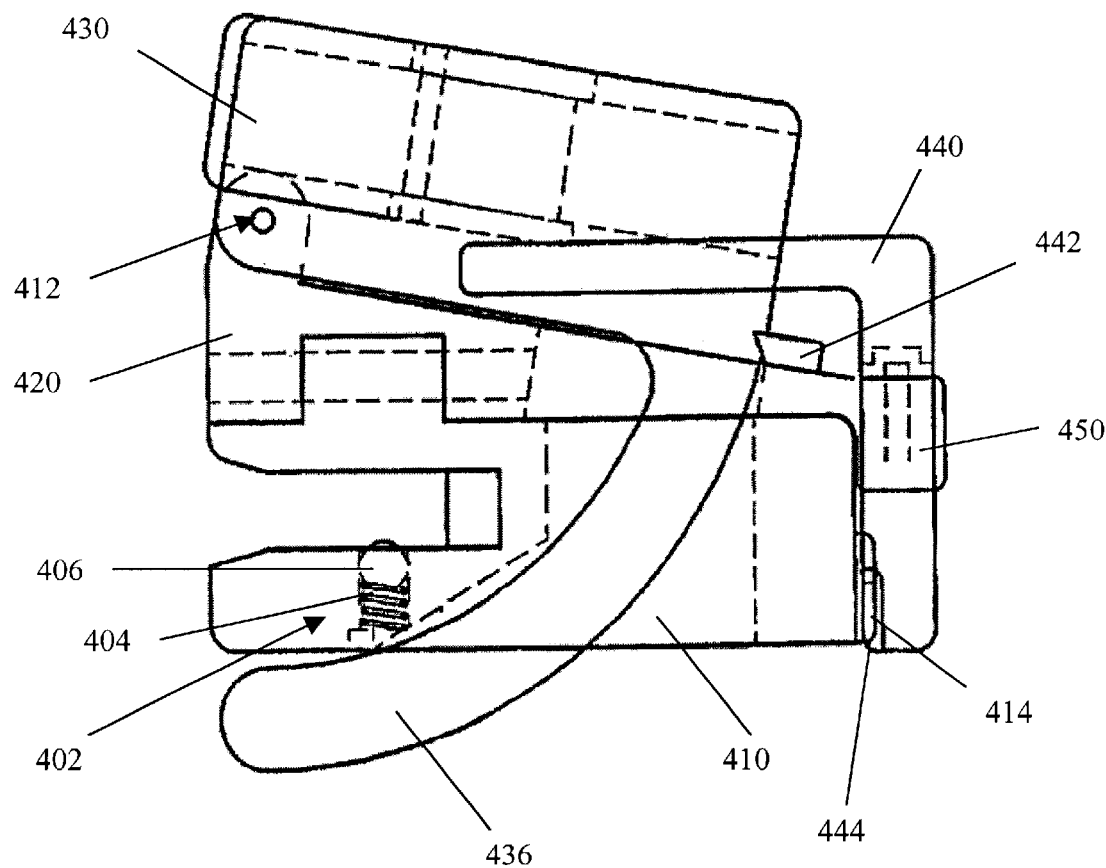
Figure 9:
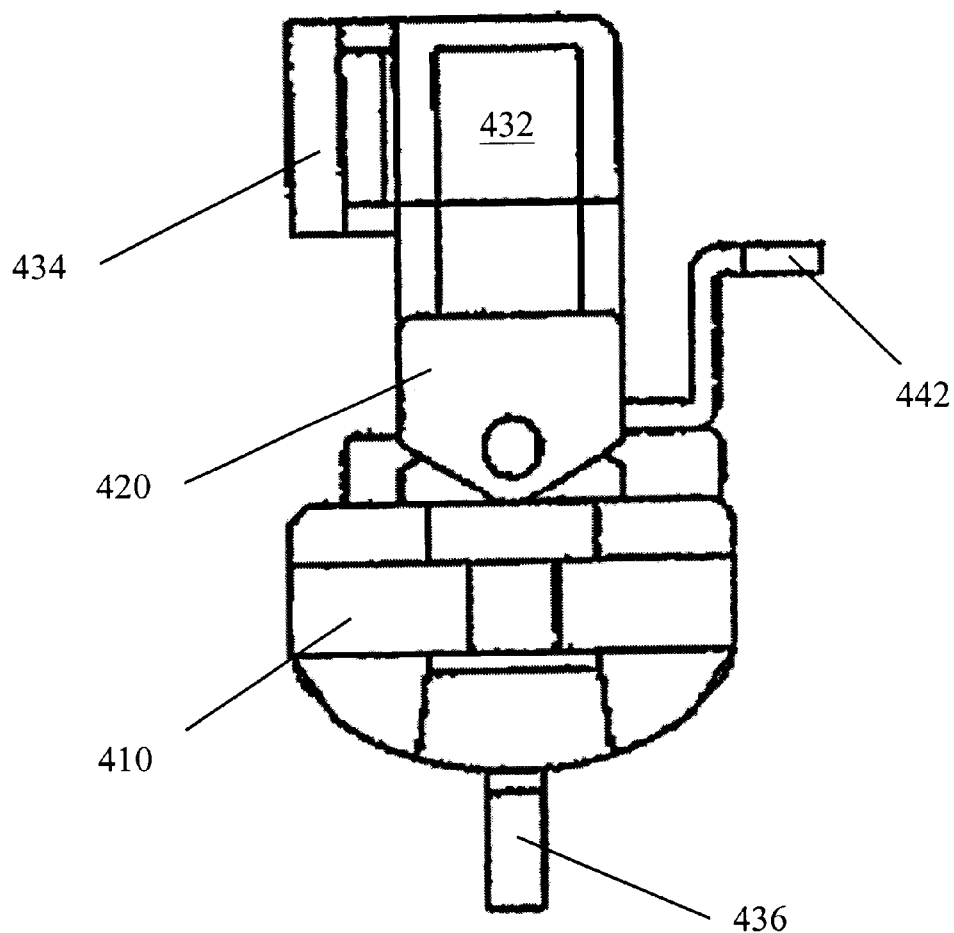
FIG. 9 is a front view of the ratchet mechanism of FIG. 7.

As shown in FIG. 9, ratchet housing 430 can be configured with an opening 432 extending lengthwise for placement of a ratcheted stem 22 therein. To control the movement of the ratchet into and out of the housing 430, ratchet housing 430 can also include a ratchet release mechanism 434 as illustrated in FIGS. 7 and 8. The ratchet release mechanism 434 can comprise a spring-biased pawl or a similarly biased hooking element as is known in the art which would enable a ratchet placed within the ratchet housing 430 to be moved forwards or backwards with precision and ease.

To effect the forwards or backwards tilting of the ratchet stem 22 and retractor blade 18 attached thereto, ratchet housing 430 can be pivotally attached to ratchet holder 420 by means of pivot mechanism 422, as shown in FIG. 8. It is contemplated that pivot mechanism 422 can comprise a pivot pin (not shown) placed through bores contained on ratchet housing 430 and ratchet holder 420. Extending from ratchet housing 420 is curved ratchet 436. A ratchet release bar 440 connected to ratchet holder 420 is provided for maintaining the ratchet 436 and ratchet housing 430 in a fixed position relative to the base member 410. Thus, the ratchet 436 can be positioned so as to be "toed-in" or "toed-out."

As shown in FIG. 9, ratchet release bar 440 is bent to provide a thumb release tab 442 at one end for manual actuation of the bar 440. The bar 440 also includes a grooved, or undercut region 444 for engaging the teeth 438 of curved ratchet 436. Ratchet release bar 440 is pivotally attached to ratchet holder 420 by connector 450 with a pivot mechanism 452 similar to the mechanism 414 described above, and can include a bar spring (not shown) for biasing against the ratchet holder 420. The release bar 440 is configured so that the tilting and locking of the ratchet housing 430 with respect to the ratchet holder 420 can be manually actuated with the thumb release tab 442 with ease.

Figure 10:
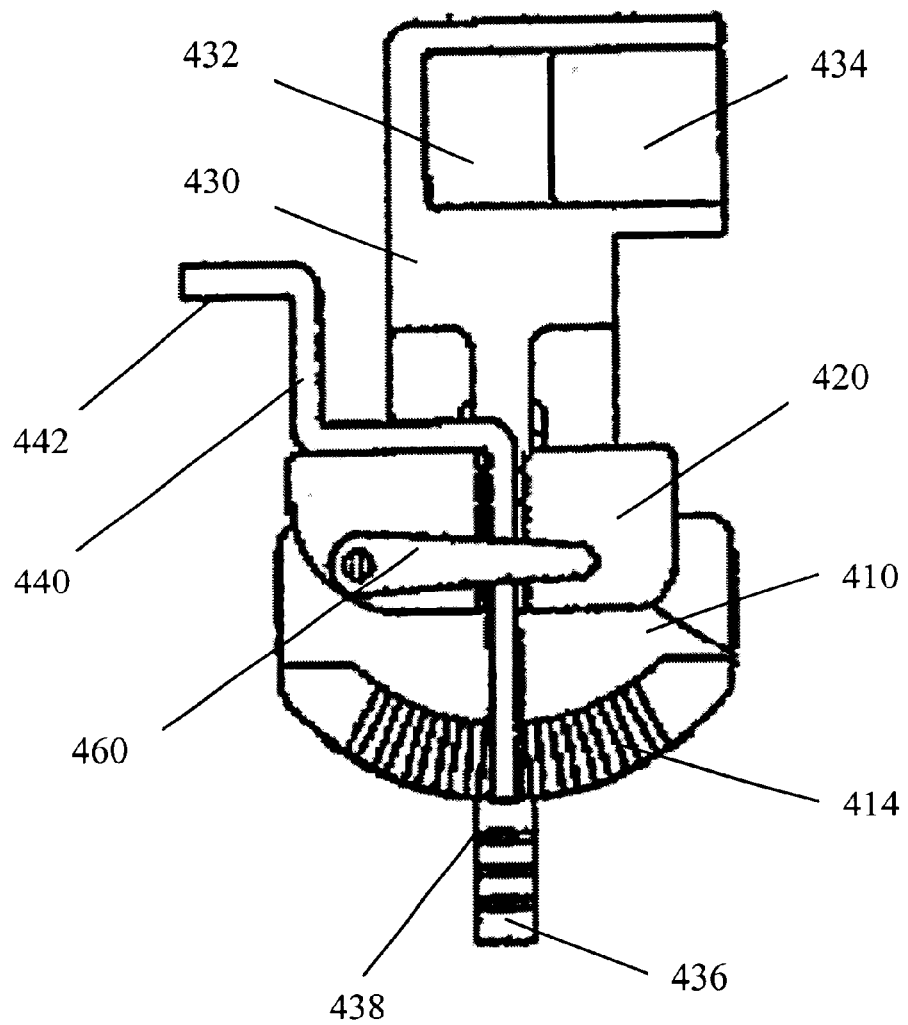
FIG. 10 is a rear view of the ratchet mechanism of FIG. 7.

In FIG. 10, the back of the ratchet mechanism 400 which is facing away from the surgical site, is shown. Base member 410 includes a plurality of indents 414 which extend in an arc along a distal-most portion of the base member 410. These indents 414 can be engaged by a cut out section or fin 444 formed on the distal-most end of the ratchet release bar 440, as shown in FIG. 8. A crossbar 460 can be included to releasably lock the ratchet release bar 440 against the indents 414, as in FIG. 10. Crossbar 460 can be pivotally attached to ratchet holder 420. The arc of indents 414 extends up to about 30 degrees to the left and to the right of the fin 444 when the fin 444 is perpendicular to the plane of circumferential ring 16. Thus, as illustrated in FIG. 7, the tilt ratchet mechanism 400 of the present invention is able to be rotated or angled up to about 30 degrees to the left or right with respect It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A device for multi-dimensional movement and placement of a retractor blade, comprising:
    a first member adapted to receive a stem of a retractor blade, the first member having a locking mechanism effective to enable selective lateral adjustment of the retractor blade relative to the first member;
    a second member to which the first member is mated, the first member being vertically pivotable with respect to the second member to enable selective vertical pivoting adjustment of the retractor blade relative to the second member; and
    a rotator indexing body mated to the second member, the second member being rotatable with respect to the rotator indexing body such that the first member, the second, housing member and the retractor blade are able to selectively rotate about the longitudinal axis of the rotator indexing body, the rotator indexing body further being adapted to mount onto a rim of a surgical support.

2. The device of claim 1, wherein the second member is rotatable up to approximately 30 degrees about the longitudinal axis of the rotator indexing body.

3. The device of claim 1, further including a ratchet release bar pivotally connected to the second member for adjustably maintaining the retractor blade a fixed vertical distance from the second member.

4. The device of claim 1, wherein the locking mechanism comprises a spring biased pawl.

5. The device of claim 1, further including a ball plunger assembly on the rotating indexer body for achieving an interference fit between the rotator indexing body and the rim of the surgical support.

6. The device of claim 1, wherein the rotator indexing body includes a plurality of indents extending circumferentially about the rotator indexing body, and a locking pin extends from the second member and engages one of the plurality of indents for maintaining the rotator indexing body in a fixed position with respect to the second member.

7. A ratchet device for positioning a retractor blade, comprising:
    a retractor blade holder having an opening therein for receiving a retractor blade and a curved ratchet extending therefrom;
    a pawl pivotally connected to the retractor blade holder for adjustably maintaining the retractor blade a fixed distance from the retractor blade holder;
    a housing member pivotally connected to the retractor blade holder and including a channel for insertion of the curved ratchet therethrough;
    a ratchet release bar pivotally connected to the housing member for adjustably maintaining the retractor blade holder a fixed distance from the housing member;
    a rotating indexer having a slot therein for attaching to a ring secured to a stationary post and further including a plurality of indents extending circumferentially about the rotating indexer, the rotating indexer being rotatably held within an opening in the housing member; and
    a locking pin extending from the housing member and engageable with the plurality of indents for maintaining the rotating indexer in a fixed position with respect to the housing member.

8. The device of claim 7, wherein the housing member is rotatable up to approximately 30 degrees about the longitudinal axis of the rotating indexer.

9. The device of claim 7, wherein the curved ratchet includes a plurality of teeth.

10. The device of claim 9, wherein the ratchet release bar includes an undercut engageable with the plurality of teeth on the curved ratchet.

11. The device of claim 7, wherein the ratchet release bar includes a thumb release tab.

12. The device of claim 7, further including a spring coil for biasing the pawl to desired position.

13. The device of claim 7, further including a spring coil for applying a spring force against ratchet release bar.

14. The device of claim 7, further including a ball plunger assembly on the rotating indexer for achieving an interference fit between the rotating indexer and an attached ring.

15. The device of claim 14, wherein the ball plunger assembly comprises a spring coil having a threaded end and a ball at an opposite end.

16. The assembly of claim 7, further including an indexer coil for exerting a spring bias force on the rotating indexer within the housing member.

* * * * *